US00PP35530P2

(12) United States Plant Patent
Spil

(10) Patent No.: US PP35,530 P2
(45) Date of Patent: Dec. 5, 2023

(54) ***ECHINACEA* PLANT NAMED 'IFECSSMIN'**

(50) Latin Name: *Echinacea hybrida*
Varietal Denomination: IFECSSMIN

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/118,458

(22) Filed: Mar. 7, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

*Primary Examiner* — Karen M Redden
(74) *Attorney, Agent, or Firm* — C. Anne Whealy

(57) ABSTRACT

A new and distinct cultivar of *Echinacea* plant named 'IFECSSMIN', characterized by its relatively compact and upright to broadly upright plant habit; moderately vigorous to vigorous growth habit; freely branching habit; strong flowering stems; numerous single-type inflorescences with orange-colored ray florets and red-colored receptacle spines; and good garden performance.

2 Drawing Sheets

Figure 1:
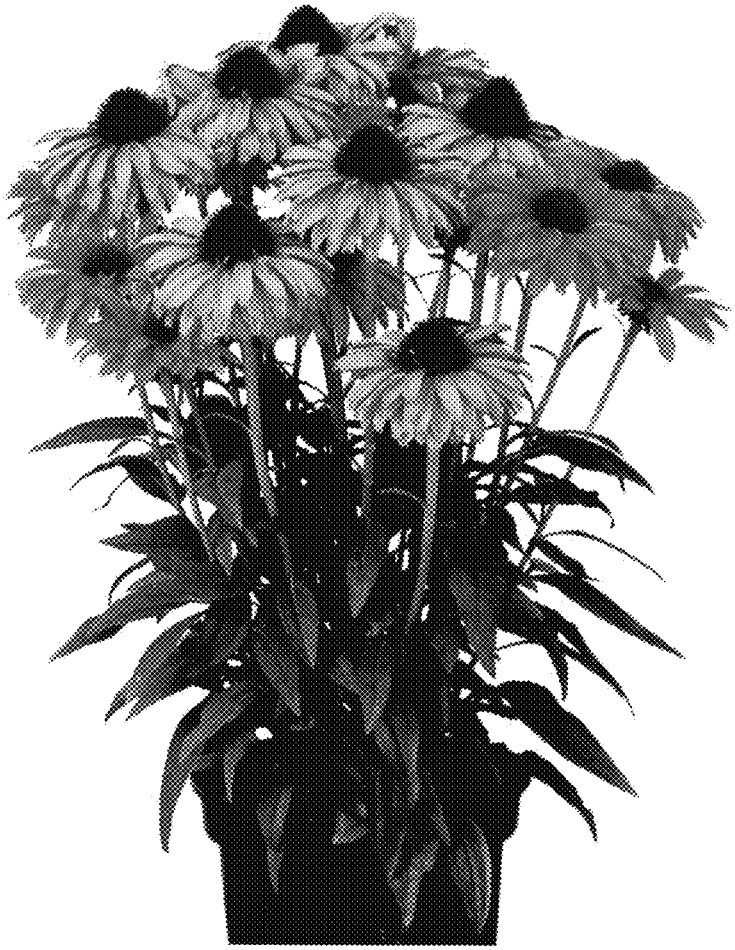

Botanical designation: *Echinacea hybrida.*
Cultivar denomination: 'IFECSSMIN'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2657. Foreign priority is not claimed to this application.

BACKGROUND OF THE INVENTION

The present invention relates to a new and distinct cultivar of *Echinacea* plant, botanically known as *Echinacea hybrida*, and hereinafter referred to by the name 'IFECSSMIN'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from an open-pollination in July, 2019 in Heerhugowaard, The Netherlands of a proprietary selection of *Echinacea hybrida* identified as code number 009-18-K057-01, not patented, as the female, or seed, parent with an unknown proprietary selection of *Echinacea hybrida*, as the male, or pollen, parent. The new *Echinacea* plant was discovered and selected by the Inventor as a single flowering plant from within the progeny of the stated open-pollination grown in a controlled greenhouse environment in Heerhugowaard, The Netherlands in August, 2020.

Asexual reproduction of the new *Echinacea* plant by in vitro meristem culture in a controlled environment in Heerhugowaard, The Netherlands since September, 2020 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSMIN'. These characteristics in combination distinguish 'IFECSSMIN' as a new and distinct *Echinacea* plant:

1. Relatively compact and upright to broadly upright plant habit.
2. Moderately vigorous to vigorous growth habit.
3. Freely branching habit.
4. Strong flowering stems.
5. Numerous single-type inflorescences with orange-colored ray florets and red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* have stronger and healthier foliage than plants the female parent selection.

3. Inflorescences of plants of the new *Echinacea* have about four whorls of ray florets whereas inflorescences of plants of the female parent selection have two whorls of ray florets.
4. Ray florets of plants of the new *Echinacea* are orange in color whereas ray florets of plants of the female parent selection are yellow in color.

Plants of the new *Echinacea* can be compared to plants of *Echinacea* spp. 'TNECHPS', disclosed in U.S. Plant Pat. No. 33,778. In side-by-side comparisons, plants of the new *Echinacea* differ primarily from plants of 'TNECHPS' in the following characteristics:

1. Plants of the new *Echinacea* are shorter and broader than plants of 'TNECHPS'.
2. Plants of the new *Echinacea* are more freely branching than plants of 'TNECHPS'.
3. Inflorescences of plants of the new *Echinacea* have about four whorls of ray florets whereas inflorescences of plants of 'TNECHPS' have two whorls of ray florets.

Plants of the new *Echinacea* can also be compared to plants of *Echinacea purpurea* 'Prima Tiger', not patented. In side-by-side comparisons, plants of the new *Echinacea* differ primarily from plants of 'Prima Tiger' in the following characteristics:

1. Plants of the new *Echinacea* are broader than plants of 'Prima Tiger'.
2. Plants of the new *Echinacea* are more freely branching than plants of 'Prima Tiger'.
3. Plants of the new *Echinacea* are more freely flowering than plants of 'Prima Tiger'.
4. Inflorescences of plants of the new *Echinacea* have about four whorls of ray florets whereas inflorescences of plants of 'Prima Tiger' have a single whorl of ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSMIN' grown in a container.

Figure 2:
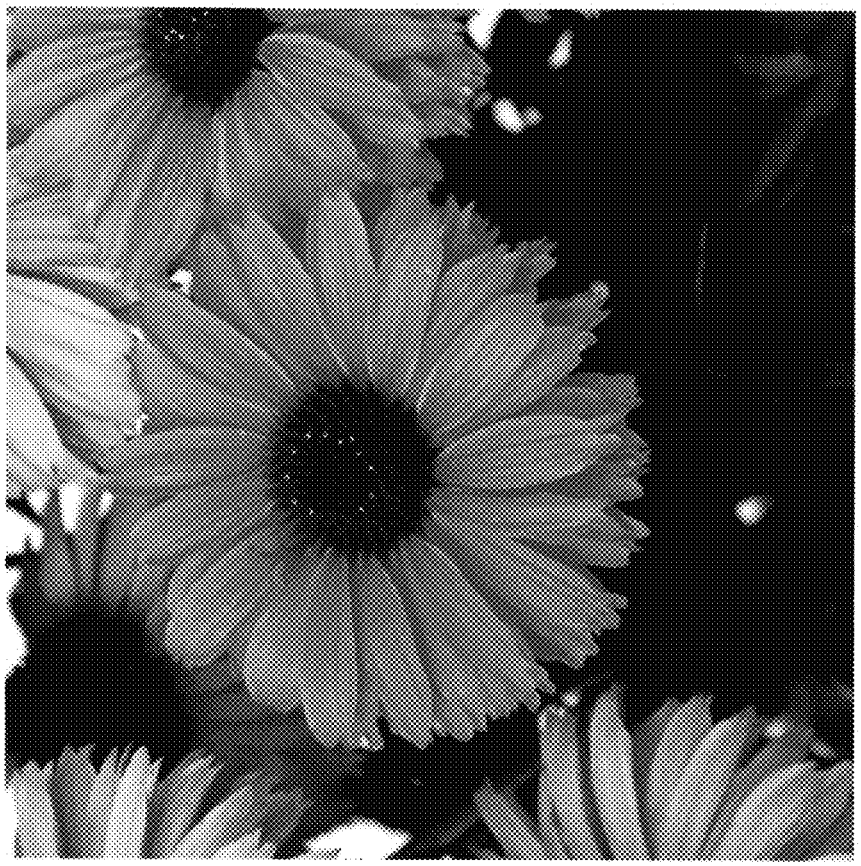

The photograph at the left of the second sheet (FIG. 2) is a close-up view of typical inflorescences of 'IFECSSMIN'.

Figure 3:
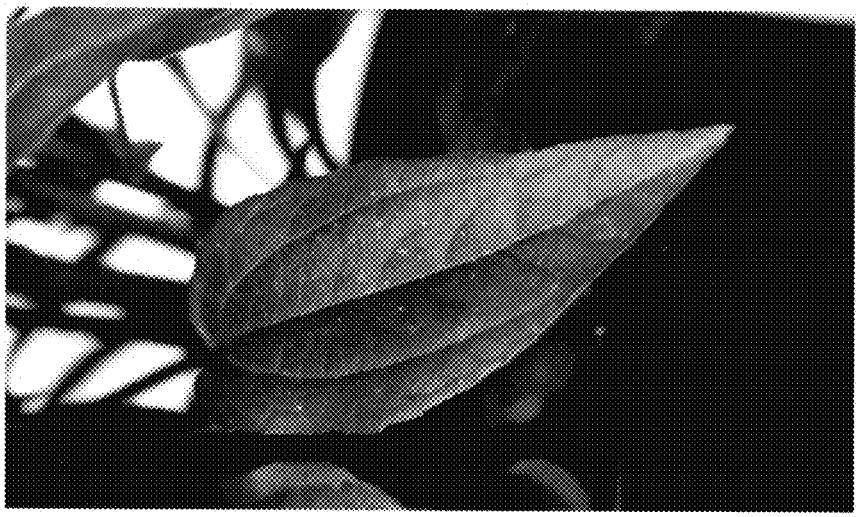

The photograph at the right of the second sheet (FIG. 3) is a close-up view of typical leaves of 'IFECSSMIN'.

DETAILED BOTANICAL DESCRIPTION

The aforementioned photographs and following observations and measurements describe plants grown during the summer in 19-cm containers in an outdoor nursery in Heerhugowaard, The Netherlands and under cultural practices typically used in commercial *Echinacea* production. During the production of the plants, day temperatures ranged from 18 C to 34 C and night temperatures ranged from 8 C to 18 C. Plants were 16 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSMIN'.

Parentage:

*Female parent*.—Proprietary selection of *Echinacea hybrida* identified as code number 009-18-K057-01, not patented.

*Male parent*.—Unknown proprietary selection of *Echinacea hybrida*, not patented.

Propagation:

*Type*.—By in vitro meristem culture.

*Time to initiate roots, summer*.—About twelve days at temperatures about 20 C.

*Time to initiate roots, winter*.—About 16 days at temperatures about 20 C.

*Time to produce a rooted young plant, summer*.—About 36 days at temperatures about 18 C.

*Time to produce a rooted young plant, winter*.—About 42 days at temperatures about 18 C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; relatively compact and upright to broadly upright plant habit; obovate in overall shape; freely basal branching habit with about eleven primary lateral branches and about ten secondary lateral branches developing per plant; moderately vigorous to vigorous growth habit and moderate growth rate.

*Plant height*.—About 45.3 cm.

*Plant diameter or spread*.—About 44 cm.

*Lateral branches*.—Length: About 22.3 cm. Diameter: About 6 mm. Internode length: About 2.7 cm. Aspect: Erect to about 15 degrees from vertical. Strength: Strong. Texture: Moderately pubescent; strigose. Color: Close to N144A; few blotches, close to 144A and 144B.

Leaf description:

*Basal and cauline leaves*.—Arrangement: Alternate, simple. Length: About 9.4 cm. Width: About 3.3 cm. Shape: Narrowly ovate. Apex: Narrowly acute. Base: Short attenuate. Margin: Mostly entire; occasionally with a few shallow and irregular indentations to irregularly shallow and broadly dentate; slightly and coarsely undulate. Texture and luster, upper and lower surfaces: Sparsely to moderately pubescent, strigose and rough; slightly glossy. Venation pattern: Pinnate. Color: Developing leaves, upper surface: Close to NN137A. Developing leaves, lower surface: Close to 146A. Fully expanded leaves, upper surface: Close to NN137A to slightly darker than NN137A; venation, close to 144B. Fully expanded leaves, lower surface: Close to a blend of 137C and 147B; venation, close to 146D.

*Petioles, basal and cauline leaves*.—Length: About 4.6 cm. Diameter: About 2 mm by 2.5 mm. Texture, upper surface: Smooth, glabrous. Texture, lower surface: Sparsely pubescent. Color, upper surface: Close to NN137A; midvein, close to 145A tinged proximally with close to 178A. Color, lower surface: Close to 137B; midvein, close to N144C.

Inflorescence description:

*Appearance*.—Single-type inflorescences with ray and disc florets arranged on a capitulum; inflorescences positioned upright above the foliar plane on mostly upright and strong peduncles.

*Flowering habit*.—Freely flowering habit with about 21 developing and fully developed inflorescences per plant.

*Fragrance*.—Faintly to moderately fragrant; sweet and pleasant.

*Time to flower*.—Plants flower continuously from late June into late September in The Netherlands.

*Inflorescence longevity*.—Inflorescences maintain good substance for about three weeks on the plant; inflorescences persistent.

*Inflorescence buds*.—Height: About 3.2 cm. Diameter: About 2.8 cm. Shape: Broadly obovate with a flattened top. Color: Immature involucral bracts, close to 143A and 143B; immature ray florets, close to N25C; immature receptacle spines, close to 152A.

*Inflorescence size*.—Diameter: About 10 cm. Depth (height): About 4.3 cm. Disc diameter: About 3.2 cm.

*Receptacles*.—Height: About 1.5 cm. Diameter: About 9 mm. Shape: Ovate. Color: Close to 155C.

*Ray florets*.—Quantity and arrangement: About 64 to 78 arranged in about four whorls at the base of the receptacle. Length: About 4.6 cm. Width: About 1.3 cm. Shape: Oblanceolate to narrowly elliptic; slightly carinate. Apex: Emarginate to praemorse. Base: Cuneate. Margin: Entire. Texture and luster, upper surface: Smooth, glabrous; moderately velvety; matte. Texture and luster, lower surface: Smooth, glabrous; slightly glossy. Aspect: About 10 degrees from horizontal; with development, apices curled slightly downward. Color: When opening, upper surface: Close to a blend of N25A and N25B. When opening, lower surface: Close to 37A and 37B. Fully opened, upper surface: Close to N25A and towards the base, close to 34A; venation, similar to lamina color; color becoming closer to N170B and towards the base, close to 176D, with subsequent development. Fully opened, lower surface: Close to 54C; venation, close to 54C; color becoming closer to 54C and 182D with apices, close to 146D, with subsequent development.

*Disc florets*.—Quantity and arrangement: About 240 per inflorescence, arranged spirally at the center of the inflorescence. Length: About 1.1 cm. Diameter: About 4 mm. Shape: Tubular; proximal 12.5% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 180A. Mid-section: Close to 148A and 148B. Base: Close to 144C. Color, fully opened, inner and outer surfaces: Apex: Close to 180A. Mid-section: Close to 148B. Base: Close to 144C.

*Receptacle spines*.—Quantity: One per disc floret; about 240 per inflorescence. Shape: Acicular. Apex: Acute. Base: Attenuate. Texture and luster: Smooth, glabrous; glossy. Color: Apex: Close to N34B with tip, close to N34A. Mid-section: Close to 143A to 143B. Base: Close to 145D.

*Involucral bracts*.—Quantity per inflorescence: About 100 arranged in about four whorls. Length: About 1.15 cm. Width: About 3 mm. Shape: Narrowly ovate; horizontal to slightly reflexed. Apex: Acute. Base: Cuneate. Margin: Entire. Texture and luster, upper surface: Smooth, glabrous; moderately glossy. Texture and luster, lower surface: Smooth, glabrous; margins, sparsely to moderately pubescent; moderately glossy. Color, upper and lower surfaces: Close to 138A; margins, close to NN137A.

*Peduncles*.—Length: About 15.8 cm. Diameter: About 4.5 cm. Strength: Strong. Aspect: Mostly upright. Texture: Sparsely pubescent; strigose. Color: Close to 146D with blotches, close to 144A.

*Reproductive organs*.—Androecium (present on ray and disc florets): Quantity per floret: Five. Filament length: About 4 mm. Filament color: Close to 150D. Anther length: About 3.5 mm. Anther shape: Linear. Anther color: Close to 200A. Pollen amount: Moderate. Pollen color: Close to 17A. Gynoecium (present only on disc florets): Quantity per floret: One. Pistil length: About 7 mm. Stigma shape: Decurrent, unequal. Stigma color: Close to 185A. Style length: About 5.5 mm. Style color: Close to 145C to 145D. Ovary color: Close to 157C. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35 C and to be hardy to USDA Hardiness Zones 3 to 4.

It is claimed:

1. A new and distinct *Echinacea* plant named 'IFECSSMIN' as illustrated and described.

* * * * *